United States Patent
Lee et al.

(10) Patent No.: US 10,577,448 B2
(45) Date of Patent: Mar. 3, 2020

(54) ORGANIC ZINC COMPOUND COMPRISING POLYOLEFIN-POLYSTYRENE BLOCK COPOLYMER, AND METHOD FOR PREPARING THE SAME

(71) Applicant: LG Chem, Ltd., Seoul (KR)

(72) Inventors: Bun Yeoul Lee, Gyeonggi-do (KR); Jong Yeob Jeon, Chungcheongnam-do (KR); Geun Ho Park, Gyeonggi-do (KR)

(73) Assignee: LG Chem, Ltd. (KR)

( * ) Notice: Subject to any disclaimer, the term of this patent is extended or adjusted under 35 U.S.C. 154(b) by 54 days.

(21) Appl. No.: 15/549,343

(22) PCT Filed: Jan. 21, 2016

(86) PCT No.: PCT/KR2016/000662
§ 371 (c)(1),
(2) Date: Aug. 7, 2017

(87) PCT Pub. No.: WO2016/129818
PCT Pub. Date: Aug. 18, 2016

(65) Prior Publication Data
US 2018/0022852 A1 Jan. 25, 2018

(30) Foreign Application Priority Data

Feb. 10, 2015 (KR) .................. 10-2015-0020432
Jan. 8, 2016 (KR) .................. 10-2016-0002924

(51) Int. Cl.
| | | |
|---|---|---|
| C08F 297/08 | (2006.01) | |
| C07F 17/00 | (2006.01) | |
| C07F 19/00 | (2006.01) | |
| C08F 112/08 | (2006.01) | |
| C08F 295/00 | (2006.01) | |
| C07F 3/06 | (2006.01) | |
| C08F 297/02 | (2006.01) | |

(52) U.S. Cl.
CPC ........... *C08F 297/083* (2013.01); *C07F 3/06* (2013.01); *C07F 17/00* (2013.01); *C07F 19/00* (2013.01); *C08F 112/08* (2013.01); *C08F 295/00* (2013.01); *C08F 297/02* (2013.01)

(58) Field of Classification Search
CPC .. C08F 297/00; C08F 297/083; C08F 297/02; C08F 295/00; C07F 3/06; C07F 19/00
See application file for complete search history.

(56) References Cited

U.S. PATENT DOCUMENTS

| | | |
|---|---|---|
| 3,887,650 A | 6/1975 | Agouri et al. |
| 3,911,054 A * | 10/1975 | Roest ........................ C08F 4/12 525/259 |
| 3,949,018 A | 4/1976 | Agouri et al. |
| 4,480,075 A * | 10/1984 | Willis .................... C08F 297/00 525/247 |
| 5,017,714 A | 5/1991 | Welborn, Jr. |
| 5,120,867 A * | 6/1992 | Welborn, Jr. ........... C07F 17/00 502/117 |
| 6,211,380 B1 | 4/2001 | Fantucci et al. |
| 2004/0236155 A1 | 11/2004 | Perichon et al. |
| 2009/0111944 A1 | 4/2009 | Kuhlman et al. |

FOREIGN PATENT DOCUMENTS

| | | |
|---|---|---|
| JP | S49132186 A | 12/1974 |
| JP | S54152094 A | 11/1979 |
| JP | S6020918 A | 2/1985 |
| JP | S6395203 A | 4/1988 |
| JP | H05125194 A | 5/1993 |
| JP | 2008533277 A | 8/2008 |
| JP | 201364088 A | 4/2013 |
| JP | 2013203879 A | 10/2013 |
| KR | 20040013110 A | 2/2004 |
| KR | 20150007484 A | 1/2015 |

OTHER PUBLICATIONS

Su, W.-F., Principles of Polymer Design and Synthesis, Chapter 9: Coordination Polymerization, Lecture Notes in Chemistry 82, pp. 219-232, Oct. 9, 2013. (Year: 2013).*
Search report from International Application No. PCT/KR2016/000662, dated Jul. 1, 2016.
Van Meurs, M., et al., "Polyethylene Chain Growth on Zinc Catalyzed by Olefin Polymerization Catalysts: A Comparative Investigation of Highly Active Catalyst Systems across the Transition Series." Journal of the American Chemical Society, Jun. 18, 2005, vol. 127, pp. 9913-9923.
Natori, Itaru, et al., "Living Anionic Polymerization of 1,3-Cyclohexadiene with the n-Butyllithium/N, N, N', N'—Tetramethylethylenediamine System. Copolymerization and Block Copolymerization with Styrene, Butadiene, and Isoprene." Macromolecules, 1998, vol. 31, No. 4., pp. 982-987.
Peinado, Carmen, et al., "Effects of ozone in surface modification and thermal stability of SEBS block copolymers." Polymer Degradation and Stability, vol. 95, 2010, pp. 975-986.

(Continued)

*Primary Examiner* — Christopher M Rodd
(74) *Attorney, Agent, or Firm* — Lerner, David, Littenberg, Krumholz & Mentlik, LLP

(57) ABSTRACT

The present invention relates to an organic zinc compound comprising a styrene-based polymer or a polyolefin-polystyrene block copolymer at both ends. Also, the present invention relates to a method for preparing the organic zinc compound, the method preparing an intermediate by coordination-polymerizing an olefin monomer using a transition metal catalyst, and then performing anionic polymerization by inserting an alkyllithium compound, an amine ligand, and a styrene-based monomer into the intermediate. Accordingly, the present invention can provide a method for preparing a commercially useful styrene-based polymer or polyolefin-polystyrene block copolymer directly from an olefin monomer and a styrene monomer in a one-pot manner.

13 Claims, 3 Drawing Sheets

(56) References Cited

OTHER PUBLICATIONS

Dong, J. Y., et al., "Synthesis of Polyethylene Containing a Terminal p-Methylstyrene Group: Metallocene-Mediated Ethylene Polymerization with a Consecutive Chain Transfer Reaction to p-Methylstyrene and Hydrogen." Macromolecules, vol. 35, 2002, pp. 1622-1631.
Ning, Fanglin, et al., "Synthesis of Amphiphilic Block-Graft Copolymers [Poly(styrene-b-ethylene-co-butylene-b-styrene)-g-Poly(acrylic acid] and Their Aggregation in Water." Journal of Polymer Science: Part A: Polymer Chemistry, vol. 40, Jan. 18, 2002, pp. 1253-1266.
Chung, T. C., et al., "A Novel Consecutive Chain Transfer Reaction to p-Methylstyrene and Hydrogen during Metallocene-Mediated Olefin Polymerization." Journal of the American Chemical Society. vol. 123, No. 21, May 30, 2001, pp. 4871-4876.
Weiser, Marc-Stephan, et al., "Marcomolecular Rapid Communications." vol. 27, 2006, pp. 1009-1014.
Carlotti, Stephane, et al., "Retarded anionic polymerization (RAP) of styrene and dienes." Polymer, vol. 50, 2009, pp. 3057-3067.
Arriola, Daniel, et al., "Catalytic Production of Olefin Block Copolymers via Chain Shuttling Polymerization." Science, vol. 312, May 5, 2006, pp. 714-719.
Deffieux, Alain, et al., "Retarded Anionic Polymerization of Styrene, 6a Influene of Zinc and Boron Derivatives on the Reactivity of Polystyryllithium." Macromolecular Chemistry and Physics, vol. 203, 2002, pp. 862-867.
Hsieh, H. L., "Effects of Diethylzinc in Alkyllithium-Initated Polymerizations." Journal of Polymer Science: Polymer Chemistry Edition, vol. 14, 1976, pp. 379-386.
Rabagliati, F. et al., "Copolymerization of styrene by diphenylzinc-additive systems. Part II: Copolymerization of styrene/1-alkene by Ph2Zn-metallo-cene-MAO systems", Polymer Bulletin, May 10, 2001, vol. 46, pp. 427-434.
Makio, H. et al., "Synthesis of Telechelic Olefin Polymers via Catalyzed Chain Growth on Multinuclear Alkylene Zinc Compounds", Journal of the American Chemical Society, May 15, 2013, vol. 135, pp. 8177-8180.
Extended European Search Report for EP16749358 dated Jan. 24, 2018.
Chinese Search Report for Application No. CN201680009628.5 dated Feb. 19, 2019.

* cited by examiner

US 10,577,448 B2

ORGANIC ZINC COMPOUND COMPRISING POLYOLEFIN-POLYSTYRENE BLOCK COPOLYMER, AND METHOD FOR PREPARING THE SAME

CROSS-REFERENCE TO RELATED APPLICATIONS

The present application is a national phase entry under 35 U.S.C. § 371 of International Application No. PCT/KR2016/000662 filed Jan. 21, 2016, which claims priority from Korean Application Nos. 10-2016-0002924 filed Jan. 8, 2016, and 10-2015-0020432 filed Feb. 10, 2015, all of which are incorporated herein by reference.

TECHNICAL FIELD

The present invention relates to an organic zinc compound comprising a polyolefin-polystyrene block copolymer and a method for preparing the same.

BACKGROUND ART

There are several hundred thousand tons of polyolefin-polystyrene block copolymers, such as styrene-ethylene/butylene-styrene (SEBS) or styrene-ethylene/propylene-styrene (SEPS) in the global market therefor. In addition, these are excellent in thermal and light resistance compared to the styrene-butadiene-styrene (SBS) or styrene-isoprene-styrene (SIS), and are used as a material for a grip and a handle with soft and good textures, a flexible material for diapers, oil-gel used for medical and communication materials, an impact modifier in engineering plastic, or a flexibilizer or toughener in transparent polypropylene. Conventional SEBS is prepared through a two-step reaction of hydrogenating SBS obtained by anionic polymerization of styrene and butadiene. Conventional SEPS is also prepared through a two-step reaction of hydrogenating SIS obtained by anionic polymerization of styrene and isoprene. Since such a process of saturating all double bonds contained in the main chain of a polymer through hydrogenation has a high production cost, the unit costs of SEBS and SEPS are considerably higher than those of SBS and SIS before hydrogenation. Such a reason may act as a limit to market expansion. In addition, since it is actually impossible to saturate all of the double bonds contained in the polymer chain through hydrogenation, commercialized SEBS and SEPS contain some remaining double bonds and the presence of the double bonds often become a problem (Journal of Polymer Science: Part A: Polymer Chemistry, 2002, 40, 1253; Polymer Degradation and Stability 2010, 95, 975). Moreover, the conventional block copolymer prepared in the two steps as described above is very limited in structure because a polyolefin block is formed by hydrogenation after anionic polymerization of butadiene or isoprene.

According to such background, the preparation of a polyolefin-polystyrene block copolymer directly through a one-pot reaction from an olefin monomer and a styrene monomer is a very challenging research topic with a large commercial ripple effect. In this context, conventionally, it has been reported that a polypropylene-polystyrene block copolymer is prepared by synthesizing polypropylene having a para-methylstyryl group at a terminal end using para-methylstyrene as a chain transfer agent in propylene polymerization from para-methylstyrene, inducing dehydrogenation of a methyl group at the terminal end using butyl lithium, and then performing anionic polymerization of styrene (J. Am. Chem. Soc. 2001, 123, 4871; Macromolecules 2002, 35, 1622). It also has been reported that there is an attempt to prepare a block copolymer by performing ethylene/propylene copolymerization using living polymerization reactivity of a phenoxyimine catalyst and subsequently injecting a styrene monomer (Macromole. Rapid. Commun., 2006, 27, 1009). However, the conventionally reported methods described above have problems of requiring multi-step processes, and thus may not be applied to a commercial process.

DISCLOSURE

Technical Problem

The present invention is directed to providing an organic zinc compound comprising a polyolefin-polystyrene block copolymer.

The present invention is directed to providing a one-pot preparation method for directly preparing the organic zinc compound comprising a polyolefin-polystyrene block copolymer from an olefin monomer and a styrene monomer.

All of the above-described and other objectives of the present invention may be achieved by the following descriptions.

Technical Solution

One aspect of the present invention provides an organic zinc compound represented by Formula 1.

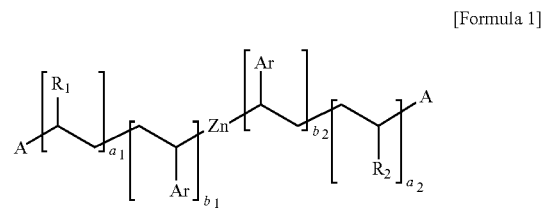

[Formula 1]

In Formula 1, $R_1$ and $R_2$ are each independently hydrogen or an alkyl group having 1 to 20 carbon atoms; Ar is an aryl group having 6 to 20 carbon atoms; A is a hydrocarbon group having 1 to 20 carbon atoms; an average value of $a_1$ and $a_2$ is approximately 0 to 10,000; and an average value of $b_1$ and $b_2$ is approximately 10 to 1,000.

$R_1$ and $R_2$ of Formula 1 may be each independently any one of hydrogen, a methyl group, an ethyl group, a butyl group, a hexyl group and an octyl group; Ar may be a phenyl group; A may be any one of a methyl group, an ethyl group, a hexyl group, a phenyl group and a benzyl group.

The organic zinc compound may be an organic zinc compound represented by Formula 1A.

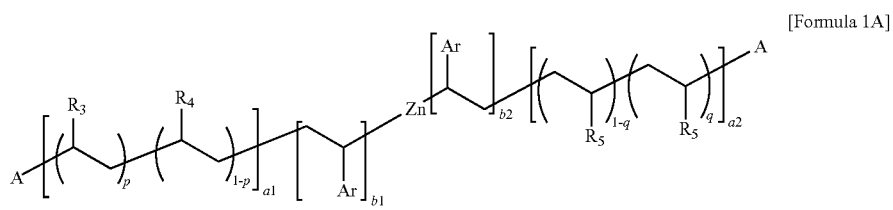

[Formula 1A]

In Formula 1A, $R_3$, $R_4$, $R_5$ and $R_6$ are each independently any one of hydrogen, a methyl group, an ethyl group, a butyl group, a hexyl group and an octyl group, $R_3$ and $R_4$ are not the same, $R_5$ and $R_6$ are not the same; Ar is a phenyl group; A is a methyl group, an ethyl group, a hexyl group, a phenyl group or a benzyl group; p and 1-p are mole fractions of respective repeating blocks constituting a repeating unit $a_1$, p ranges from approximately more than 0 and less than 1; q and 1-q are mole fractions of respective repeating blocks constituting a repeating unit $a_2$, q ranges from approximately more than 0 less than 1; an average value of $a_1$ and $a_2$ is approximately more than 0 to 10,000; and an average value of $b_1$ and $b_2$ is approximately 10 to 1,000.

Any one of $R_3$ and $R_4$ of Formula 1A may be hydrogen, and the other one may be a methyl group, an ethyl group, a butyl group or a hexyl group; any one of $R_5$ and $R_6$ may be hydrogen, and the other one may be a methyl group, an ethyl group, a butyl group or a hexyl group.

Another aspect of the present invention provides a method for preparing the above-described organic zinc compound. The method for preparing the organic zinc compound includes a first step of preparing a compound represented by Formula 3 through coordination polymerization of an olefin monomer using a transition metal catalyst in the presence of organic zinc represented by Formula 2; and a second step of sequentially adding an alkyl lithium compound represented by Formula 4, an amine ligand represented by Formula 5 and a styrene-based monomer to the compound represented by Formula 3 to perform anionic polymerization.

$(A)_2Zn$      [Formula 2]

In Formula 2, A is a hydrocarbon group having 1 to 20 carbon atoms;

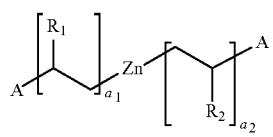

[Formula 3]

In Formula 3, $R_1$ and $R_2$ are each independently hydrogen or an alkyl group having 1 to 20 carbon atoms; A is a hydrocarbon group having 1 to 20 carbon atoms; and an average value of $a_1$ and $a_2$ is approximately 0 to 10,000;

B—Li      [Formula 4]

In Formula 4, B is an alkyl group having 1 to 20 carbon atoms;

[Formula 5]

In Formula 5, $R^{51}$ and $R^{52}$ are each independently a hydrocarbon group having 1 to 20 carbon atoms, and z is an integer of approximately 2 or 3.

The olefin monomer ($CH_2$=CH—R) may be ethylene, propylene, 1-butene, 1-hexene, 1-octene, 1-decene or a mixture thereof, and the styrene-based monomer (ArCH=$CH_2$) may be styrene.

The olefin monomer ($CH_2$=CH—R) may be a mixture of any one of propylene, 1-butene, 1-hexene and 1-octene, and ethylene, and the styrene-based monomer (ArCH=$CH_2$) may be styrene.

In Formula 2, A may be any one of a methyl group, an ethyl group, a hexyl group, a phenyl group and a benzyl group.

The transition metal catalyst may include a transition metal compound represented by Formula 6A or Formula 6B below.

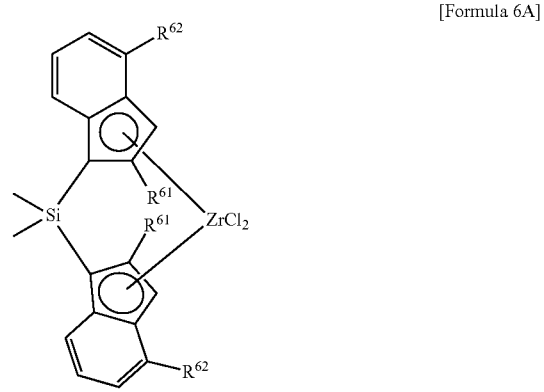

[Formula 6A]

In Formula 6A, $R^{61}$ is hydrogen or methyl, and $R^{62}$ is hydrogen or phenyl;

[Formula 6B]

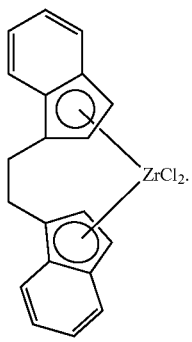

The polymerization of the first step may be performed by solution polymerization using a solvent containing one or more of isobutane, hexane, cyclohexane and methylcyclohexane.

The alkyl lithium compound may be n-BuLi.

The amine ligand represented by Formula 5 may be a compound in which $R^{51}$ is methyl, $R^{52}$ is hydrogen, and z is 2.

A molar ratio of the alkyl lithium compound and the amine ligand may be approximately 1:0.5 to 1:1.5.

Advantageous Effects

The present invention has an effect of providing a method for directly preparing a commercially available styrene-based polymer or polyolefin-polystyrene block copolymer from an olefin monomer and a styrene monomer in "one-pot."

MODES OF THE INVENTION

Organic Zinc Compound Comprising Block Copolymer

Figure 1:
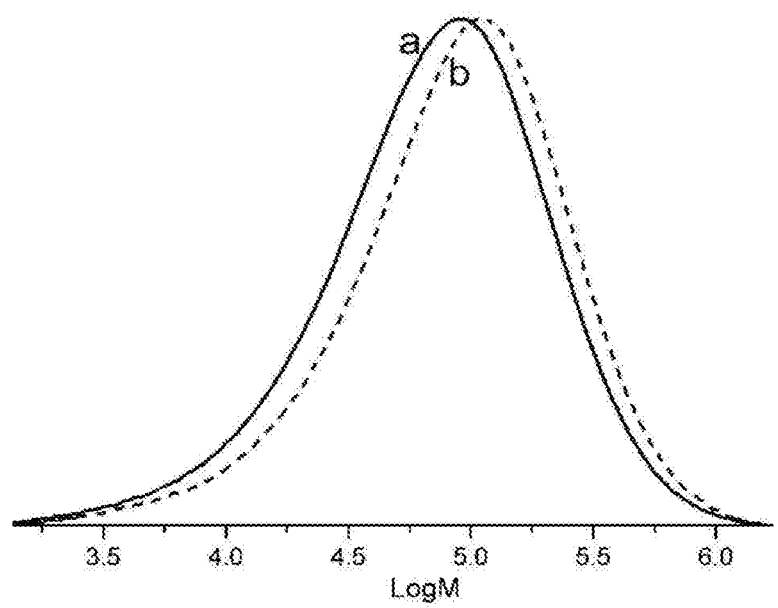
FIG. 1 is a graph showing GPC analysis results of a polyolefin sample obtained in a first step and a polyolefin-polystyrene copolymer prepared by both a first step and a second step according to Example 15 of the present invention.

An exemplary embodiment of the present invention relates to an organic zinc compound represented by Formula 1.

[Formula 1]

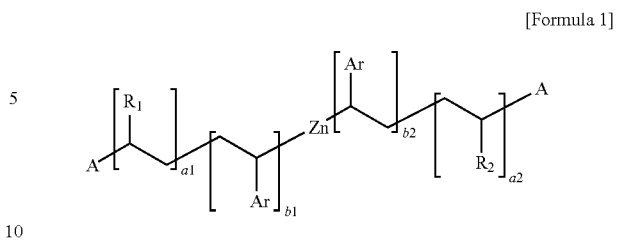

In Formula 1, $R_1$ and $R_2$ are each independently hydrogen or an alkyl group having 1 to 20 carbon atoms; Ar is an aryl group having 6 to 20 carbon atoms; A is a hydrocarbon group having 1 to 20 carbon atoms; an average value of $a_1$ and $a_2$ is approximately 0 to 10,000; and an average value of $b_1$ and $b_2$ is approximately 10 to 1,000.

The organic zinc compound represented by Formula 1 is a compound first revealed according to the preparation method of the present invention, which comprises a polyolefin-polystyrene block copolymer in its structure. The organic zinc compound represented by Formula 1 can react with water, oxygen or an organic acid to be easily converted into an industrially useful polyolefin-polystyrene block copolymer having a structure represented by Formula 7 below.

[Formula 7]

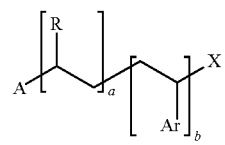

(X is H or OH)

In Formula 7, R is specifically hydrogen or an alkyl group having 1 to 20 carbon atoms, and more specifically, any one of hydrogen, methyl, ethyl, butyl, hexyl and octyl, and in this case, the compound has low unit cost and production cost, and therefore may be more excellent in industrial availability.

A block copolymer prepared using the organic zinc compound represented by Formula 1 may be, for example, polyethylene-block-polystyrene, polypropylene-block-polystyrene, poly(1-butene)-block-polystyrene, poly(1-hexene)-block-polystyrene, or poly(1-octene)-block-polystyrene.

In the specification, the repeating units $a_1$ and $a_2$ in the square brackets ([ ]) refer to polyolefin blocks constituting the block copolymer. Likewise, the repeating units $b_1$ and $b_2$ in square brackets ([ ]) of the formula refer to polystyrene blocks constituting the block copolymer. The repeating units may be composed of repeating blocks derived from one or more monomers.

In the specification, the $a_1$, $a_2$, $b_1$ and $b_2$ may be marks discriminating repeating units (or respective blocks), and also used as marks indicating the number of repeating unit repetitions. Through conventional polymer synthesis, a mixture in which the $a_1$, $a_2$, $b_1$ and $b_2$ values have a predetermined distribution, not single integers, is obtained, and then the average value is calculated.

The average value of $a_1$ and $a_2$ of Formula 1 can be modulated according to contents of the olefin monomer and the organic zinc compound, which are added to the reactants. While there is no limitation to the lower limit of the average value of $a_1$ and $a_2$, when the average value of $a_1$ and $a_2$ is approximately more than 10,000, due to a high viscosity, a preparation method is difficult to carry out, and thus it is difficult to realize the compound having the structure of Formula 1. Specifically, the average value of $a_1$ and $a_2$ in Formula 1 may be approximately 0 to 10,000.

The average value of $b_1$ and $b_2$ in Formula 1 can be modulated according to a content of the styrene monomer added to the reactants. When the average value of $b_1$ and $b_2$ is approximately more than 10,000, due to a high viscosity, a preparation method is difficult to carry out. In addition, when the b value is approximately less than 10, it is difficult to realize the block copolymer having the structure of Formula 1. Specifically, $b_1$ and $b_2$ in Formula 1 may be approximately 10 to 1,000. In this range, the block copolymer may be applied to more various fields, and its preparation method is more effective.

Specifically, the repeating units $a_1$ and $a_2$ in Formula 1 may be prepared by using an olefin monomer having an alkyl group having 1 to 20 carbon atoms as a material for preparing the organic zinc compound of Formula 1. In an exemplary embodiment, the repeating units $a_1$ and $a_2$ may be prepared by using an olefin monomer such as ethylene, propylene, 1-butene, 1-hexene, 1-octene, or 1-decene as a reactant.

The repeating units $b_1$ and $b_2$ of Formula 1 may be prepared by specifically using a styrene-based monomer as a reactant. In an exemplary embodiment, the repeating units $a_1$ and $a_2$ may be prepared using a styrene-based monomer such as ethylene substituted with a C6 to C20 aryl group or ethylene substituted with a phenyl group as a reactant.

The terminal end A of Formula 1 is derived from an organic group (A) containing organic zinc ((A)$_2$Zn) represented by Formula 2 added according to a method for preparing an organic zinc compound which will be described below. Specific examples of (A)$_2$Zn include dimethyl zinc, diethyl zinc, dihexyl zinc, diphenyl zinc, and dibenzyl zinc. Such compounds may be commercially available or easily prepared, and thus may improve efficiency of preparing the organic zinc compound of Formula 1.

In one exemplary embodiment, $R_1$ and $R_2$ of Formula 1 are each independently any one of hydrogen, a methyl group, an ethyl group, a butyl group, a hexyl group and an octyl group; Ar is a phenyl group; and A may be any one of a methyl group, an ethyl group, a hexyl group, a phenyl group and a benzyl group. In this case, the organic zinc compound may exhibit more excellent reaction efficiency, and using the compound, a polyolefin-polystyrene block copolymer having a large commercial ripple effect and a method for preparing the same may be provided.

In one exemplary embodiment, the repeating units $a_1$ and $a_2$ of Formula 1 may include, for example, as shown in Formula 1A, one or more (e.g., two) of olefin repeating blocks.

[Formula 1A]

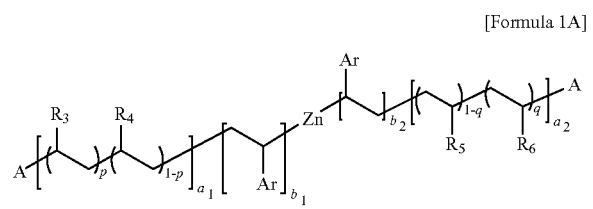

In Formula 1A, $R_3$, $R_4$, $R_5$ and $R_6$ are each independently any one of hydrogen, a methyl group, an ethyl group, a butyl group, a hexyl group and an octyl group, $R_3$ and $R_4$ are not the same, $R_5$ and $R_6$ are not the same; Ar is a phenyl group; A is a methyl group, an ethyl group, a hexyl group, a phenyl group or a benzyl group; p and 1-p are mole fractions of respective repeating blocks constituting the repeating unit $a_1$, p is approximately more than 0 and less than 1; q and 1-q are mole fractions of respective repeating blocks constituting the repeating unit $a_2$, q is approximately more than 0 and less than 1; an average value of $a_1$ and $a_2$ is approximately more than 0 to 10,000; and an average value of $b_1$ and $b_2$ is approximately 10 to 1,000.

The organic zinc compound represented by Formula 1A reacts with water, oxygen or an organic acid to be easily converted into an industrially useful polyolefin-polystyrene block copolymer.

In Formula 1A, $R_3$, $R_4$, $R_5$ and $R_6$ may be randomly dispersed in the repeating units $a_1$ and $a_2$ (polyolefin block).

In Formula 1A, the repeating unit $a_1$ may contain the olefin repeating units p and 1-p. In the specification, p and 1-p are used as markers for discriminating olefin repeating blocks constituting the repeating unit $a_1$, and refer to mole fractions of the repeating blocks p and 1-p in the repeating unit $a_1$, respectively. A polyolefin block in which two repeating blocks (p and 1-p) are randomly distributed may be prepared using two olefins selected from ethylene, propylene, 1-butene, 1-hexene, 1-octene and 1-decene as reactants.

Likewise, in Formula 1A, the repeating unit $a_2$ may include repeating blocks q and 1-q. In the specification, q and 1-q are used as markers for discriminating the olefin repeating blocks constituting the repeating unit $a_2$, and refer to mole fractions of the repeating blocks q and 1-q in the repeating unit $a_2$, respectively. A polyolefin block in which the two repeating blocks (q and 1-q) are randomly distributed may be prepared using two olefins selected from ethylene, propylene, 1-butene, 1-hexene, 1-octene and 1-decene as reactants.

In one exemplary embodiment, any one of $R_3$ and $R_4$ of Formula 1A may be hydrogen, and the other one may be a methyl group, an ethyl group, a butyl group or a hexyl group; any one of $R_5$ and $R_6$ may be hydrogen, and the other one may be a methyl group, an ethyl group, a butyl group or a hexyl group. In this case, the organic zinc compound represented by Formula 1A may be used to provide polyolefin-polystyrene block copolymers having various structures, which conventionally had limitations in being commercially prepared, with further excellent productivity.

The block copolymer prepared using the organic zinc compound represented by Formula 1A may be, for example, poly(ethylene-co-propylene)-block-polystyrene, poly(ethylene-co-1-butene)-block-polystyrene, poly(ethylene-co-1-hexene)-block-polystyrene, or poly(ethylene-co-1-octene)-block-polystyrene.

Method for Preparing Organic Zinc Compound Comprising Block Copolymer

Another exemplary embodiment of the present invention relates to a method for preparing the above-described organic zinc compound of Formula 1.

According to the method for preparing an organic zinc compound comprising a polyolefin-polystyrene block copolymer of the present invention, the above-described organic zinc compound of Formula 1 is prepared using an olefin monomer and a styrene monomer as reactants. The organic zinc compound of Formula 1 prepared by such a method may react with water, oxygen, or an organic acid to be easily converted into a polyolefin-polystyrene block copolymer having an industrially useful structure.

In addition, the method for preparing an organic zinc compound of the present invention is a one-pot preparation method, which can easily obtain a polyolefin-polystyrene block copolymer only with a simple process of continuously adding water, oxygen or an organic acid to the preparation method, but excludes a saturation process of separately hydrogenating the block copolymer. Likewise, the organic zinc compound of Formula 1, prepared by the one-pot process, and the method for preparing the same are first disclosed by the present invention.

As described above, when the organic zinc compound of Formula 1 and the method for preparing the same are applied to prepare the block copolymer, the prepared polyolefin block may be prepared in various types without limitation to the structure of a polyolefin block which will be prepared, and therefore the present invention is a very useful technique for preparing a block copolymer suitable for a use and a purpose.

The method for preparing the organic zinc compound of Formula 1 of the present invention provides the organic zinc compound in a one-pot preparation method, and continuously prepares a polyolefin-polystyrene block copolymer from the organic zinc compound of Formula 1 by the one-pot preparation method. For this reason, this method is simple, and thus is advantageous for commercialization.

The method for preparing an organic zinc compound comprising a polyolefin-polystyrene block copolymer includes a first step of preparing a compound represented by Formula 3 through coordination polymerization of an olefin monomer with a transition metal catalyst in the presence of organic zinc represented by Formula 2 below; and a second step of continuously adding an alkyl lithium compound represented by Formula 4 below, an amine ligand represented by Formula 5 below, and a styrene-based monomer to the compound represented by Formula 3 to perform anionic polymerization.

(A)$_2$Zn     [Formula 2]

In Formula 2, A is a hydrocarbon group having 1 to 20 carbon atoms;

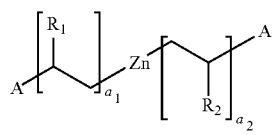     [Formula 3]

In Formula 3, R$_1$ and R$_2$ are each independently hydrogen or an alkyl group having 1 to 20 carbon atoms; A is a hydrocarbon group having 1 to 20 carbon atoms; and the average value of a$_1$ and a$_2$ is approximately 0 to 10,000;

B—Li     [Formula 4]

In Formula 4, B is an alkyl group having 1 to 20 carbon atoms;

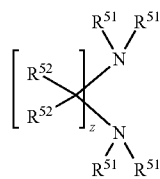     [Formula 5]

In Formula 5, R$^{51}$ and R$^{52}$ are each independently a hydrocarbon group having 1 to 20 carbon atoms, and z is an integer of approximately 2 or 3.

First Step of Preparing Compound Represented by Formula 3

The compound represented by Formula 3, prepared in the first step, may be prepared through coordination polymerization of an olefin monomer that will be described below with a transition metal catalyst in the presence of organic zinc represented by Formula 2.

Specifically, the olefin monomer added as the reactant in the first step may be an alpha olefin having 1 to 20 carbon atoms (CH$_2$=CH—R). More specifically, as the olefin monomer, a monomer formed of ethylene, propylene, 1-butene, 1-hexene, 1-octene, 1-decene or a mixture thereof may be used. One of the olefin monomers may be used alone, or two or more thereof may be used in combination.

Another specific example of the olefin monomer may be a monomer formed of a mixture of any one of propylene, 1-butene, 1-hexene and 1-octene with ethylene. Such polyolefin prepared from any one of propylene, 1-butene, 1-hexene and 1-octene, and ethylene may be, for example, HDPE, MDPE, LLDPE, VLDPE, POE or EP.

In Formula 2, A may be any one of a methyl group, an ethyl group, a hexyl group, a phenyl group and a benzyl group. In an exemplary embodiment, when, as the olefin monomer, ethylene, propylene or 1-butene, which has a relatively low boiling point, is used, polymerization may be performed under a predetermined pressure.

Specifically, the organic zinc represented by Formula 2 may be a dimethyl zinc, diethyl zinc, dihexyl zinc, diphenyl zinc, or dibenzyl zinc compound. Such a compound may be commercially available and also easily prepared.

While there is no specific limitation to the transition metal catalyst used in the first step, conventionally, a homogeneous (methallocene) catalyst, or heterogeneous Ziegler catalyst, which includes a transition metal catalyst as a main catalyst and/or an organic aluminum or boron compound as a cocatalyst, may be used. In the exemplary embodiment, the homogeneous catalyst is preferable due to a higher catalytic activity.

The process of the first step for preparing the organic zinc compound represented by Formula 3 through olefin polymerization using various transition metal catalysts in the presence of organic zinc ((A)$_2$Zn) is commercially available to prepare a precisely controlled polyolefin chain by a previously known method (J. AM. CHEM. SOC. 2005, 127, 9913; Science 2006, 312, 714). Previously known methods may be used for the polymerization of the first step according to the present invention.

Specifically, the transition metal catalyst may include a compound represented by Formula 6A or 6B.

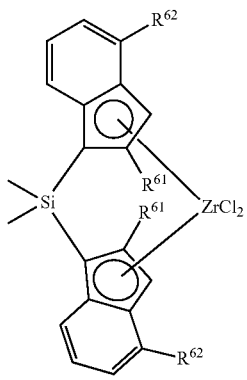

[Formula 6A]

In Formula 6A, $R^{61}$ is hydrogen or methyl, and $R^{62}$ is hydrogen or phenyl;

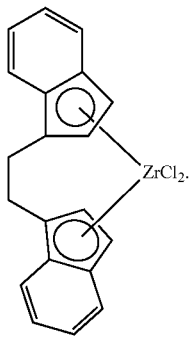

[Formula 6B]

In Formula 6A, $R^{61}$ is hydrogen or methyl; and $R^{62}$ is hydrogen or phenyl.

When the compound represented by Formula 6A or 6B is used as the transition metal catalyst, the above-described organic zinc ($(A)_2Zn$) may be more effective in conversion of the above-described organic zinc ($(A)_2Zn$) into the compound represented by Formula 3. In addition, the transition metal catalyst may be activated by methylaluminoxane (MAO) or a boron-based cocatalyst.

In the preparation method according to an exemplary embodiment, the coordination polymerization in the first step may be performed in a homogeneous solution. Here, a hydrocarbon solvent may be used as a solvent or an olefin monomer may be used as a medium. As the hydrocarbon solvent, an aliphatic hydrocarbon solvent having 4 to 20 carbon atoms, specifically, isobutane, hexane, cyclohexane, or methylcyclohexane may be used. One type of the solvent may be used alone, or two or more types of the solvents may be used in combination.

A temperature for the polymerization in the first step may vary depending on reactants, reaction conditions, etc., but may, specifically, range from approximately 70° C. to 170° C. In this range, a solubility of the polymer may be increased, and a catalyst may be thermally stabilized.

The polymerization in the first step may be performed in a batch manner, semi-continuous manner or continuous manner, and may also be performed in two or more steps which have different reaction conditions.

The compound represented by Formula 3 prepared in the first step according to the above-described examples serves as a precursor for preparing the above-described organic zinc compound represented by Formula 1 by anionic polymerization in the second step, which will be described below.

In one exemplary embodiment, according to the method for preparing the organic zinc compound of the present invention, in the first step, the organic zinc compound in which both of $a_1$ and $a_2$ of Formula 1 are approximately 0 may be prepared by excluding the addition of an olefin monomer. In this case, an organic zinc compound comprising a styrene-based polymer, not a polyolefin-polystyrene block copolymer, may be obtained by continuously performing the second step which will be described below.

Second Step of Performing Anionic Polymerization

The above-described organic zinc compound comprising the organic zinc compound of Formula 1 may be prepared by continuously performing a second step, following the first step for preparing the above-described compound represented by Formula 3.

In the second step, a styrene-based monomer may be continuously inserted between zinc-carbon bonds in the compound of Formula 3 formed in the first step as described above. Accordingly, the organic zinc compound comprising a block copolymer of the present invention may be prepared by a one-pot preparation method. In addition, the organic zinc compound prepared by the process reacts with water, oxygen or an organic acid to be converted into an industrially useful polyolefin-polystyrene block copolymer.

It is a well-known fact that organic zinc ($(A)_2Zn$) does not autonomously serve as an initiator in styrene polymerization. That is, following the coordination polymerization in the first step, when the styrene monomer is only added, the polymerization reaction does not progress at all. In addition, when styrene polymerization is performed using alkyl lithium as an initiator in the presence of an organic zinc compound ($(A)_2Zn$) in a hydrocarbon solvent, a polymer chain is formed only from an alkyl lithium compound. The organic zinc compound still remains without participating in chain polymerization (Comparative Example 1), which is also well known (Polymer, 2009, 50, 3057).

In the second step of the present invention, following the coordination polymerization in the first step, anionic polymerization is performed by adding an alkyl lithium compound and an amine ligand of Formula 5 which will be described below as initiators. That is, anionic polymerization is performed by continuously adding an alkyl lithium compound, an amine ligand represented by Formula 5 below and a styrene-based monomer to the compound represented by Formula 3, thereby preparing the organic zinc compound comprising the block copolymer represented by Formula 1.

Specifically, the styrene-based monomer may be an alpha styrene-based monomer ($ArCH=CH_2$) having 6 to 20 carbon atoms. More specifically, the styrene-based monomer may be a styrene-based monomer, such as styrene, including ethylene substituted with an aryl group having 6 to 20 carbon atoms, or ethylene substituted with a phenyl group.

Specifically, the alkyl lithium compound may be a compound represented by Formula 4 below.

$$B\text{—}Li \qquad \text{[Formula 4]}$$

In Formula 4, B is an alkyl group having 1 to 20 carbon atoms.

More specifically, B—Li may be n-BuLi. n-BuLi is a material widely used as an initiator for anionic polymerization, which is easily obtained and has excellent unit cost efficiency.

According to the preparation method according to examples of the present invention, a polystyrene-based block may be formed by continuously inserting a styrene-based monomer between zinc-carbon bonds in the compound represented by Formula 3 by adding the amine ligand represented by Formula 5 below with the above-described alkyl lithium compound, and such a method is a novel process which has not been conventionally known in the art.

[Formula 5]

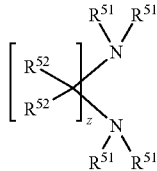

In Formula 5, $R^{5'}$ and $R^{52}$ are each independently a hydrocarbon group having 1 to 20 carbon atoms, and z is an integer of approximately 2 or 3.

Specifically, the compound of Formula 5 may be a compound (N,N,N',N'-tetramethylethylenediamine, TMEDA) in which $R^{51}$ is methyl, $R^{52}$ is hydrogen, and z is 2. Such a compound of Formula 5 is a compound which is easily coordinated to lithium and used to improve reactivity as a base of alkyl lithium or reactivity as a nucleophile and easily obtained, and has a low unit cost.

In one exemplary embodiment, the compound of Formula 5 may be added in a molar ratio of approximately 1:0.5 to 1:1.5, for example, 1:1, with respect to the alkyl lithium compound (B—Li).

Specifically, the alkyl lithium compound and the compound of Formula 5 may be mixed in an aliphatic hydrocarbon solvent and then added, or the alkyl lithium compound and the compound of Formula 5 may be sequentially added to a reactor.

In the present invention, an organic zinc compound comprising the block copolymer of Formula 1 may be prepared by performing olefin polymerization in the first step and anionic polymerization in the second step. Conventionally, an extremely small amount of the transition metal catalyst used for the olefin polymerization in the first step does not affect the anionic polymerization in the second step, compared to the alkyl lithium compound added in the second step. However, when further added to the olefin polymerization in the first step, an organic aluminum-based cocatalyst is used at a considerable amount relative to the amount of the alkyl lithium compound added to the second step. Conventionally, the organic aluminum compound forms a complex with the alkyl lithium compound, and is actually used as a reaction rate inhibitor in the anionic polymerization of styrene (Polymer, 2009, 50, 3057). That is, when the anionic polymerization in the second step is performed after the first step performed using the organic aluminum compound as a cocatalyst, it is preferable that the number of moles of the alkyl lithium compound added corresponds to the sum of the number of moles of aluminum contained in the organic aluminum compound added in the first step and approximately 0.15 to 0.25 times the number of moles of the organic zinc of Formula 2.

In one exemplary embodiment, due to the presence of the organic zinc compound ($A_2Zn$) of Formula 2, the second step may be performed without performing the olefin polymerization in the first step. The organic zinc compound produced thereby is a compound in which a is 0 in Reaction Scheme 1. The alkyl lithium compound may be added at approximately 0.1 to 1.0 times the number of moles of the organic zinc compound ($A_2Zn$). More preferably, the alkyl lithium compound may be added at approximately 0.15 to 0.25 times the amount of the organic zinc compound. When the amount of the added alkyl lithium compound is too small, an anionic polymerization rate is decreased, which is not preferable, and when the amount of the added alkyl lithium compound is too large, the amount of polystyrene determined from the alkyl lithium compound may be increased, which is not preferable.

The polymerization temperature in the second step may vary depending on reactants, reaction conditions, etc., but preferably may be approximately 70° C. to 170° C. In this range, a yield of the organic zinc compound comprising the block copolymer represented by Formula 1 may be further improved.

The polymerization in the second step may be performed in a batch manner, a semi-continuous manner or a continuous manner, or may also be performed in two or more steps which have different reaction conditions.

A polymerization time in the second step may vary depending on reactants, reaction conditions, etc., but preferably is approximately 0.5 to 10 hours, 0.5 to 8 hours, 0.5 to 5 hours, or 0.5 to 2 hours. In this range, a conversion ratio of converting the added styrene-based monomer into the organic zinc compound comprising the block copolymer may be increased.

The present invention is characterized by providing an organic zinc compound of Formula 1 subjected to the olefin polymerization in the first step, followed by continuous anionic polymerization of styrene in "one-pot," and therefore simplifies a method for preparing a block copolymer, reduces a production cost, and thus is easily applied to a commercial-scale process.

Hereinafter, configurations and actions of the present invention will be described in further detail with reference to exemplary examples of the present invention. However, these examples are merely provided as preferable examples, and it is to be understood that the present invention is not limited to the following examples by any means.

EXAMPLES

Example 1: Preparation of Organic Zinc Compound [Formula 1 (a=0, A=Hexyl, Ar=pH)] Containing Polystyrene Group After a dihexyl zinc compound (11.3 mg, 0.048 mmol) was dissolved in methylcyclohexane (2.5 g) in a one-neck flask, a solution prepared by dissolving n-BuLi (6.2 mg, 0.096 mmol, =0.20) and a compound of Formula 5, TMEDA (11.2 mg, 0.096 mmol) in methylcyclohexane (2.5 g) at a molar ratio of 1:1 was added thereto. After stirring for 10 minutes, a styrene monomer (2.5 g, 24 mmol, [Styrene]/[Zn]=500) was dissolved in methylcyclohexane (2.5 g) and then added, followed by anionic polymerization for 2 hours at 90° C. Conversion of all of the styrene into polystyrene was identified by an NMR spectrum.

An organic zinc compound comprising polystyrene and an organic lithium compound prepared thereby were decomposed by adding ethanol (1 mL), and dissolved in methylcyclohexane, then passed through a silica gel pad to obtain pure polystyrene. The obtained pure polystyrene has a mass corresponding to the amount of the added styrene monomer. The molecular weight of the obtained polystyrene was measured by gel permeation chromatography, and thus a number average molecular weight (Mn) was 25,100. The number of polystyrene polymer chains produced from the organic zinc compound may be calculated from the measured Mn by the following equation.

The number of polystyrene polymer chains produced from the organic zinc compound={[PS-chains]-[Li]}/[Zn]= [styrene]/[Zn]/DP-[n-BuLi.TMEDA]/[Zn] where DP=$M_n$/104)

The number of polystyrene polymer chains produced from the organic zinc compound was 1.87, demonstrating that the polystyrene chains did not only develop from n-BuLi.(TMEDA) added as an initiator, but were also effectively grown from the organic zinc compound. When the calculated {[PS-chains]-[Li]}/[Zn] value was 2.0, the polystyrene chains were effectively grown in two directions from all of n-BuLi and the added dihexyl zinc compound, indicating that all of the added organic zinc compound (A-Zn-A) was converted into the compound of Formula 1 (a=0) (Reaction Scheme 1).

In addition, after a reaction in the solution produced by polymerization was terminated with ethanol, gas chromatography was performed to detect hexane, thereby identifying that almost no hexane was detected, which also demonstrates that the polymer chains were effectively grown in two directions from the zinc compound.

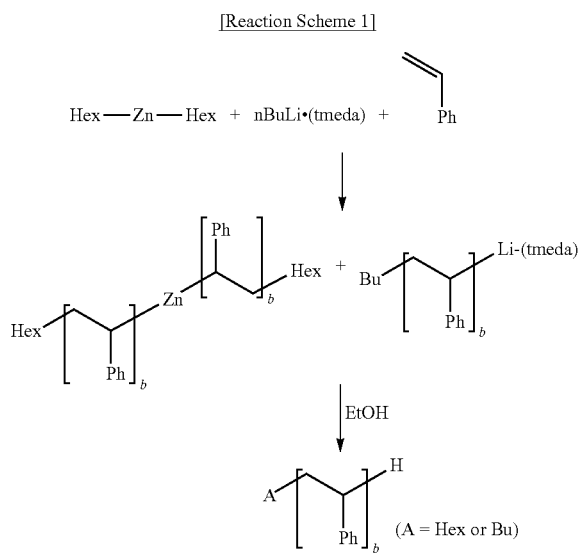

[Reaction Scheme 1]

Example 2

An experiment was performed by the same method as described in Example 1, except that an amount of n-BuLi.(TMEDA) was increased 5 times (i.e., [Li]/[Zn]=1.0). The number of polystyrene polymer chains (i.e., {[PS-chains]-[Li]}/[Zn]) produced from an organic zinc compound was 1.97, confirming that the polymer chains were effectively grown in two directions from the zinc compound.

Example 3

An experiment was performed by the same method as described in Example 1, except that an amount of n-BuLi.(TMEDA) was decreased by ½ (i.e., [Li]/[Zn]=0.10). While a reaction time required for converting all of the styrene monomer was 8 hours, the number of polystyrene polymer chains (i.e., {[PS-chains]-[Li]}/[Zn]) produced from the organic zinc compound was 1.89, confirming that polymer chains were effectively grown in two directions from the zinc compound.

Examples 4 to 7

An experiment was performed by the same method as described in Example 1, except that an amount of a styrene monomer (i.e., [styrene]/[Zn]) was increased from 500 to 600, 700, 800, or 900. The number of polystyrene polymer chains (i.e., {[PS-chains]-[Li]}/[Zn]) produced from the organic zinc compound ranged from 1.84 to 2.16, confirming that the polymer chains were effectively grown in two directions from the zinc compound.

Examples 8 to 9

An experiment was performed by the same method as described in Example 1, except that an amount of a styrene monomer (i.e., [styrene]/[Zn]) was reduced from 500 to 400 or 300. The number of polystyrene polymer chains produced from the organic zinc compound (i.e., {[PS-chains]-[Li]}/[Zn]) was 1.52 and 1.39, which were slightly off from a desired value 2.0. It means that the polymer chains were not grown from all Zn-hexyl groups of the added dihexyl zinc compound, but the polymer chains were grown from 76% and 70% of the added Zn hexyl groups and thereby the structure of Formula 1 is produced with considerable efficiency.

Comparative Example 1

An experiment was performed by the same method as described in Example 2, except that n-BuLi, instead of n-BuLi.(TMEDA), was used as an initiator. An Mn of the produced polymer was 52,900, the number of polystyrene polymer chains (i.e., {[PS-chains]-[Li]}/[Zn]) produced from the organic zinc compound, calculated therefrom, was 0, indicating that the polymer chains were not grown from the organic zinc compound at all (Reaction Scheme 2). This corresponds to the reported results (Polymer 2009, 50, 3057; Macromolecular Chemistry and Physics 2002, 203, 862; Journal of Polymer Science: Polymer Chemistry Edition 1976, 14, 379). That is, when only an alkyl lithium compound was added without using both the alkyl lithium compound and an amine ligand represented by Formula 5, the polymer chains were not grown from the added organic zinc compound (A-Zn-A) and thus a desired organic zinc compound with attached polystyrene, represented by Formula 1, was not produced. The present invention is characterized by adding both the alkyl lithium compound and the amine ligand represented by Formula 5, growing the polymer chains from the added organic zinc compound (A-Zn-A), thereby preparing the organic zinc compound with the attached polystyrene group, represented by Formula 1. The following Reaction Scheme 2 effectively shows a reaction scheme of Comparative Example 1.

[Reaction Scheme 2]

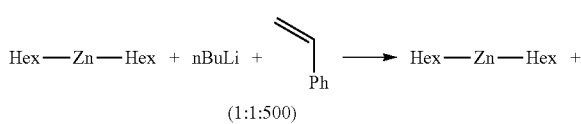

(1:1:500)

-continued

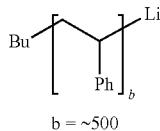

b = ~500

The following Table 1 shows the results of the organic zinc compounds prepared according to Examples 1 to 9 and Comparative Example 1.

TABLE 1

|  | [Styrene]/[Zn] | [n-BuLi · TMEDA]/[Zn] | Reaction time (h) | $M_n$ | $Mw/M_n$ | {[PS-chains]-[Li]}/[Zn] |
|---|---|---|---|---|---|---|
| Example 1 | 500 | 0.20 | 2 | 25100 | 1.52 | 1.87 |
| Example 2 | 500 | 1.0 | 2 | 18000 | 1.26 | 1.89 |
| Example 3 | 500 | 0.10 | 8 | 27900 | 1.54 | 1.97 |
| Example 4 | 600 | 0.20 | 2 | 30600 | 1.47 | 1.84 |
| Example 5 | 700 | 0.20 | 2 | 32900 | 1.49 | 2.01 |
| Example 6 | 800 | 0.20 | 2 | 35600 | 1.47 | 2.14 |
| Example 7 | 900 | 0.20 | 3 | 39600 | 1.50 | 2.16 |
| Example 8 | 400 | 0.20 | 2 | 24200 | 1.49 | 1.52 |
| Example 9 | 300 | 0.20 | 2 | 19600 | 1.43 | 1.39 |
| Comparative Example 1 | 500 | 1.0 (w/o TMEDA) | 2 | 52900 | 1.18 | 0 |

Example 10: Preparation of Organic Zinc Compound [Formula 1 (R=H, Ar=pH, A=Hexyl)] Containing Polyethylene-Block-Polystyrene Group First step: (Hex)$_2$Zn (47.1 mg, 200 µmol) was dissolved in methylcyclohexane (20 g) and added to a high pressure reactor, and then heated to 60° C. An activating solution in which (EBI)ZrCl$_2$ (1.5 µmol, Formula 6B) and MMAO (250 µmol) were mixed in methylcyclohexane (1 mL) was injected into the reactor, and then ethylene was directly charged under 30 bar and after one minute, continuously injected into the reactor at a rate of 230 ml/min for 1 hour. The pressure was adjusted to a level ranging from 15 to 20 atm.

Second step: Methylcyclohexane (10 g) was added to reduce a viscosity of the solution, and a temperature was adjusted to 110° C. n-BuLi (18.6 mg, 290 µmol, [Li]=[Al]+0.2×[Zn]) and TMEDA (33.7 mg, 290 µmol) were dissolved in methylcyclohexane (1 g) and added to a high pressure reactor, and following stirring for 15 minutes, styrene (10.4 g, 100 mmol, [styrene]/[Zn]=500) was injected. Anionic polymerization was performed for 2 hours at 120° C., and 1H NMR analysis was performed on some samples to confirm that all styrene monomers were consumed.

After the temperature was reduced to a room temperature, the produced organic zinc compound comprising a block copolymer group was transferred to a flask, chloroform (80 mL) and 2N hydrochloric acid (2 mL) were added and then stirred for 2 hours to decompose the organic zinc compound while refluxing, and methanol (80 mL) was added to precipitate a polymer material. The polymer material was dispersed in ethyl acetate (150 mL), stirred for 1 hour while refluxing, and filtered after acetone (150 mL) was added, so as to isolate a polystyrene homopolymer and a block copolymer. Solid materials separated by filtration were dried in a vacuum oven (130), thereby obtaining the block copolymer. Polymer materials remaining after a solvent was removed from the filtrate were dried in a vacuum oven (130), thereby obtaining the polystyrene homopolymer.

Examples 11 and 12

Polymerizations in first and second steps were performed by the same method as described in Example 10, except that the amount of an organic zinc compound ((Hex)$_2$Zn) was increased to 300 µmol or 400 µmol, the amounts of n-BuLi and TMEDA were increased to 310 µmol or 330 µmol, and the amount of styrene was increased to 15.6 or 20.8 g ([styrene]/[Zn]=500), and a block copolymer and a PS-homopolymer were isolated also by the same method as described above.

In Tables 2 and 3, the prepared organic zinc compounds comprising a polyethylene-polystyrene block copolymer group of Examples 10 to 12 were summarized and listed.

TABLE 2

| Example | (Hex)$_2$Zn (µmol) | MAO (Al-µmol) | n-BuLi (µmol) | Converted monomer | |
|---|---|---|---|---|---|
|  |  |  |  | $C_2H_4$ (g) | styrene (g) |
| 10 | 200 | 250 | 290 | 21.3 | 10.4 |
| 11 | 300 | 250 | 310 | 22.3 | 15.6 |
| 12 | 400 | 250 | 330 | 19.9 | 20.8 |

TABLE 3

| Example | Extracted PS (g (%)) | Extracted PS-$M_n$ (PDI)(kDa) | Number of anion chains (µmol) | PO-$M_w$ (PDI)(kDa) | Block copolymer-$M_w$ (PDI)(kDa) |
|---|---|---|---|---|---|
| 10 | 4.1 (39) | 16.3 (1.60) | 638 | 65.2 (3.75) | 83.6 (4.81) |
| 11 | 6.2 (40) | 18.3 (1.64) | 852 | 54.1 (3.62) | 71.9 (4.58) |
| 12 | 7.9 (38) | 17.7 (1.64) | 1175 | 46.5 (3.92) | 66.8 (4.38) |

In Tables 2 and 3, it was confirmed that, compared to a weight average molecular weight (PO-Mw) of the polyethylene sample taken after the first step, a weight average molecular weight (block copolymer-Mw) of the polymer obtained after the anionic polymerization in the second step was continuously performed was increased, which shows that the organic zinc compound comprising a block copolymer group is formed (Reaction Scheme 3). Particularly, the increment of the molecular weight (DMw, 18000, 18000, 20000) almost corresponds to the molecular weight of the extracted polystyrene-homopolymer (16000, 18000, 18000), which may show that the block copolymer is efficiently formed. Also, moles of polystyrene chain growth points (638 µmol, 852 µmol and 1175 µmol) in the anionic polymerization, calculated from the extracted PS-Mn value, almost correspond to the sum of moles of the added n-BuLi and double the moles of the added organic zinc compound (650 μmol, 910 μmol and 1130 μmol), which can show that, in the anionic reaction in the second step, the polystyrene chains were efficiently grown in two directions from the organic zinc compound of Formula 3 (R=H) formed in the first step.

[Reaction Scheme 3]

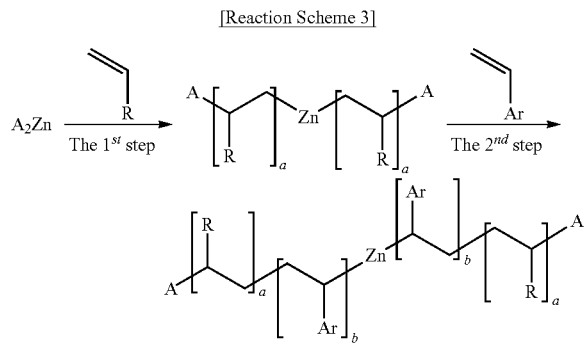

Example 13: Preparation of Organic Zinc Compound Containing Poly(Ethylene-Co-1-Octene)-Block-Polystyrene Group [Formula 1A ($R^1$=H, $R^2$=Hexyl, Ar=Ph, A=benzyl)]

First step: (benzyl)$_2$Zn (49.6 mg, 200 μmol) and 1-octene (5 g) were dissolved in methylcyclohexane (20 g) and added to a high pressure reactor, and then heated to 60° C. An activated solution in which rac-[Me$_2$Si(2-methylindenyl)]$_2$ZrCl$_2$(SBI) (1.0 μmol, Formula 6A) and MMAO (200 μmol) are mixed in methylcyclohexane (1 mL) was injected into the reactor, ethylene was directly charged under 30 bar, and then one minute later, continuously injected at a speed of 230 ml/min for 40 minutes. The pressure was adjusted to a level ranging from 5 to 10 atm.

Second step: methylcyclohexane (10 g) was added to reduce a viscosity of the solution and a temperature was adjusted to 110° C. n-BuLi (15.4 mg, 240 μmol, [Li]=[Al]+ 0.20×[Zn]) was dissolved in methylcyclohexane (1 g), injected into a high pressure reactor, stirred for 15 minutes, and then TMEDA (27.9 mg, 240 μmol) was dissolved in methylcyclohexane (1 g) to be continuously added to the high pressure reactor. After stirring for 15 minutes, styrene (10.4 g, 100 mmol, [styrene]/[Zn]=500) was injected. After anionic polymerization was performed for 3 hours at 120° C., 1H NMR analysis was performed on some samples to confirm that all styrene monomers were consumed. A polystyrene homopolymer and a block copolymer were isolated by the same method as described in Example 10.

Examples 14 and 15

Polymerizations in first and second steps were performed by the same method as described in Example 13, except that the amount of an organic zinc compound ((benzyl)$_2$Zn) was increased to 300 μmol or 400 μmol, the amounts of n-BuLi and TMEDA were increased to 260 μmol or 280 μmol, and the amount of styrene was increased to 15.6 or 20.8 g ([styrene]/[Zn]=500), and a block copolymer and a PS-homopolymer were isolated by the same method as described above.

Examples 16 to 18

Polymerization in first and second steps were performed by the same method as described in Example 13, except that the amount of 1-octene in the first step was increased to 10 g, and ethylene was continuously injected at a speed of 150 mL/min for 40 minutes. In addition, a block copolymer and a PS-homopolymer were isolated by the same method as described above.

In Tables 4 and 5, the organic zinc compounds comprising a block copolymer group prepared in Examples 13 to 18 are summarized and listed.

TABLE 4

| Example | (Benzyl)$_2$Zn (μmol) | MMAO (Al-μmol) | BuLi (μmol) | Oct (g) | Converted monomer $C_2H_4$ (g) | styrene (g) |
|---|---|---|---|---|---|---|
| 13 | 200 | 200 | 240 | 5 | 17.3 | 10.4 |
| 14 | 300 | 200 | 260 | 5 | 19.2 | 15.6 |
| 15 | 400 | 200 | 280 | 5 | 18.5 | 20.8 |
| 16 | 200 | 200 | 240 | 10 | 15.8 | 10.4 |
| 17 | 300 | 200 | 260 | 10 | 10.8 | 15.6 |
| 18 | 400 | 200 | 280 | 10 | 13.4 | 20.8 |

TABLE 5

| Example | Extracted PS (g (%)) | Extracted PS-$M_n$ (PDI)(kDa) | Number of anionic chains (μmol) | PO-$M_w$ (PDI) (kDa) | Block copolymer-$M_w$ (PDI)(kDa) |
|---|---|---|---|---|---|
| 13 | 3.8 (36) | 22.0 (1.97) | 473 | 174 (4.30) | 193 (4.04) |
| 14 | 5.1 (33) | 21.2 (1.59) | 736 | 138 (4.30) | 158 (3.52) |
| 15 | 5.3 (25) | 23.0 (1.76) | 904 | 110 (3.92) | 131 (2.90) |
| 16 | 3.7 (36) | 21.1 (1.69) | 493 | 131 (4.03) | 150 (3.10) |
| 17 | 5.3 (34) | 21.3 (1.55) | 732 | 91 (3.24) | 113 (2.76) |
| 18 | 5.3 (25) | 22.5 (1.86) | 924 | 77 (3.37) | 87 (2.73) |

In Tables 4 and 5, it was confirmed that, compared to a weight average molecular weight (PO-Mw) of the polyethylene sample taken after the first step, a weight average molecular weight (block copolymer-Mw) of the polymer obtained after the anionic polymerization in the second step was continuously performed was increased, which shows that the organic zinc compound comprising a block copolymer group is formed (Reaction Scheme 3). Particularly, the increment of the molecular weight (DMw, 19000, 20000, 21000, 19000, 22000, or 10000) almost corresponds to the molecular weight (22000, 21000, 23000, 21000, 21000, or 23000) of the extracted polystyrene-homopolymer, which may show that the block copolymer is efficiently formed. Also, a fraction (36%, 33%, 25%, 36%, 34%, 25%) of the PS-homopolymer extracted from total PS almost corresponds to the theoretical value ([n-BuLi]/[n-BuLi]+2× [Zn])= 38%, 30%, 26%, 38%, 30%, 26%1, which can show that an organic zinc compound comprising a block copolymer group of Formula 1A ($R^1$=H, $R^2$=hexyl, Ar=Ph, A=benzyl) is efficiently produced from Formula 3 through the anionic polymerization in the second step.

FIG. 1 shows molecular weight distribution curves obtained through GPC analyses for the polyolefin sample taken after the first step in Example 15 of the present invention and the polyolefin-polystyrene copolymer isolated from the organic zinc compound prepared through both of the first and second steps.

Figure 2:
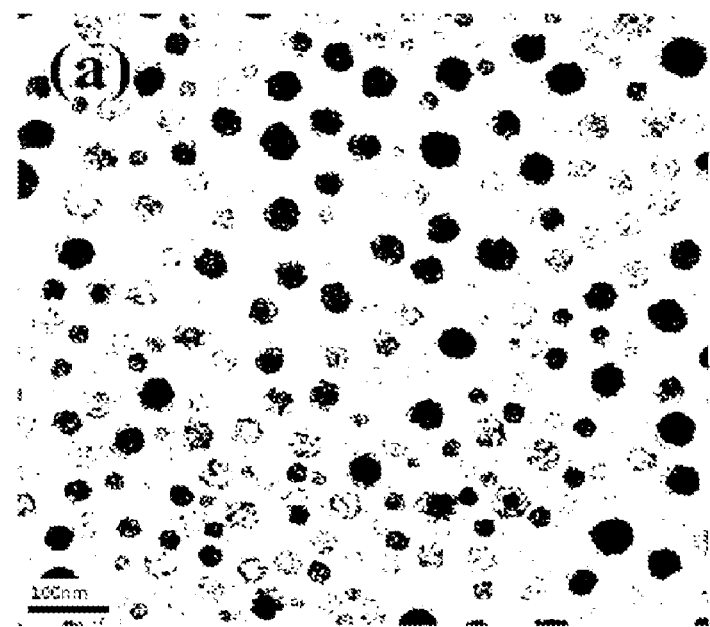
FIG. 2 is a TEM image of a polyolefin-polystyrene block copolymer prepared in Example 13 of the present invention.
Figure 3:
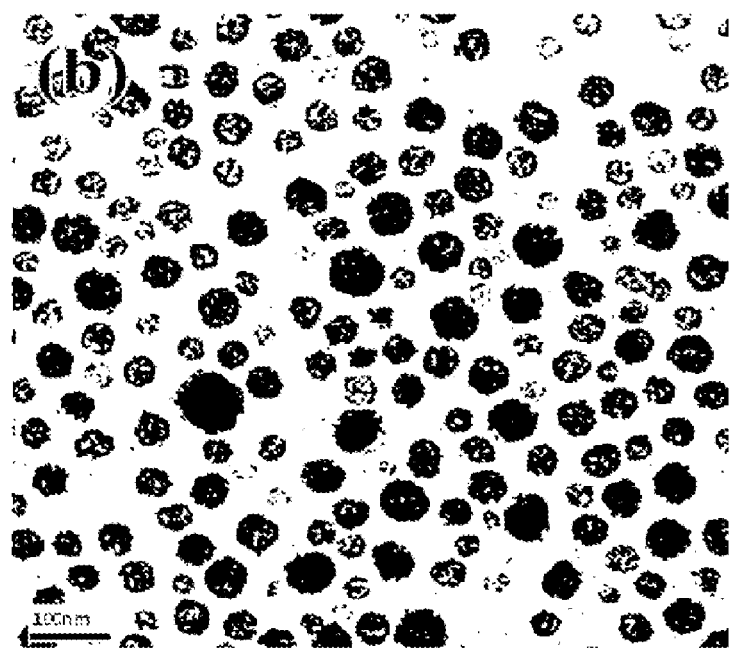
FIG. 3 is a TEM image of a polyolefin-polystyrene block copolymer prepared in Example 14 of the present invention.
Figure 4:
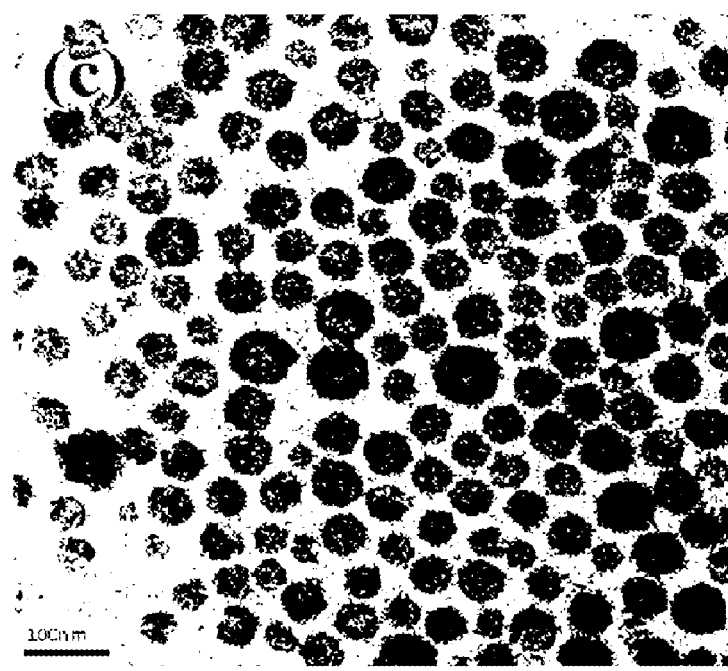
FIG. 4 is a TEM image of a polyolefin-polystyrene block copolymer prepared in Example 15 of the present invention.
Figure 5:
FIG. 5 is a TEM image of a blend having the same molecular weight as the polyolefin-polystyrene block copolymer prepared in Example 15 of the present invention.

FIGS. 2 to 4 show TEM images of poly(ethylene-co-1-octene)-block-polystyrene block copolymers prepared according to Example 13 (FIG. 2), Example 14 (FIG. 3), Example 15 (FIG. 4). FIG. 5 shows a TEM image of a blend obtained by mixing each block in the block copolymer of Example 15 with poly(ethylene-co-1-octene) and polystyrene at the same molecular weights and ratios.

These TEM images may be stained with $RuO_4$ to see a black polystyrene domain.

As seen from FIGS. 2 to 5, it can also be confirmed from the TEM images of the copolymers prepared using the organic zinc compounds of Examples 13 to 15 of the present invention that, compared to the TEM image (FIG. 5) of the blend, smaller polystyrene domains are uniformly distributed, demonstrating that a block copolymer is formed.

Figure 6:
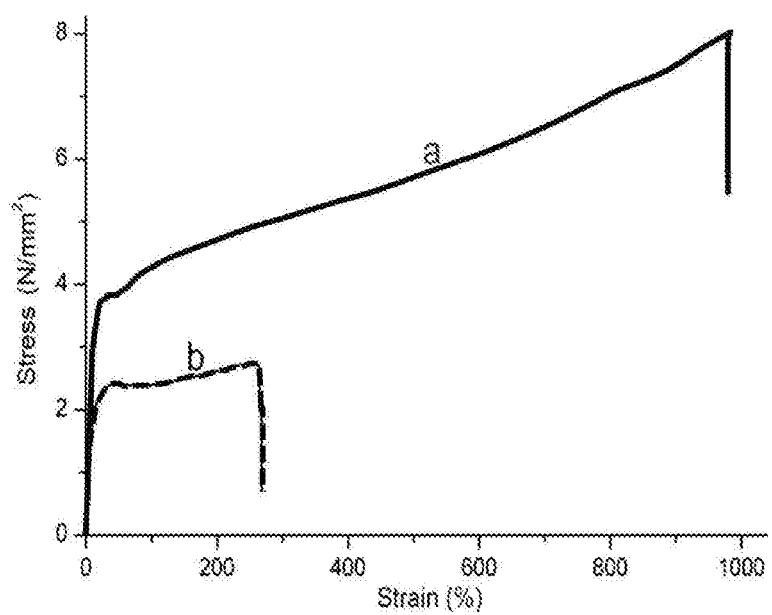
FIG. 6 is a diagram showing a stress-strain curve for a polyolefin-polystyrene block copolymer prepared in Example 16 of the present invention and a blend having the same molecular weight as the block copolymer.

FIG. 6 shows a stress-strain curve (a) of the poly(ethylene-co-1-octene)-block-polystyrene block copolymer prepared according to Example 16 and a stress-strain curve (b) of the blend obtained by mixing poly(ethylene-co-1-octene) and polystyrene at the same molecular weights and ratios as the blocks of the block copolymer of Example 16. It can also be shown that, compared to the blend, the polymer prepared in Example 16 has a 2.7 times higher tensile strength (2.85 $N/mm^2$ and 7.89 $N/mm^2$) and also has a noticeably higher percentage of elongation (270% and 970%), which is further demonstrated that the block copolymer is formed.

It will be understood by those skilled in the art that simple changes or modifications may be easily made, and are considered to be included in the scope of the present invention.

The invention claimed is:

1. A method for preparing an organic zinc compound represented by Formula 1 below, the method comprising:
   a first step of preparing a compound represented by Formula 3 through coordination polymerization of an olefin monomer using a transition metal catalyst in the presence of organic zinc represented by Formula 2; and
   a second step of sequentially adding an alkyl lithium compound represented by Formula 4, an amine ligand represented by Formula 5 and a styrene-based monomer to the compound represented by Formula 3 to perform anionic polymerization;
   wherein a ratio of an amount of the amine ligand to an amount of the organic zinc is from 0.2 to 1.0;
   wherein a ratio of an amount of the styrene-based monomer to an amount of the organic zinc is from 500 to 900;
   wherein the transition metal catalyst is a homogeneous catalyst; and
   wherein the organic zinc represented by Formula 2 is converted into the organic zinc compound of Formula 1:

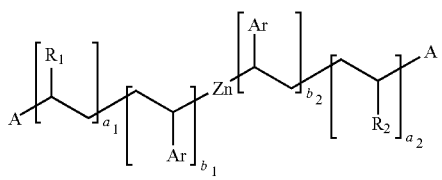
[Formula 1]

where $R_1$ and $R_2$ are each independently hydrogen or an alkyl group having 1 to 20 carbon atoms; Ar is an aryl group having 6 to 20 carbon atoms; A is a hydrocarbon group having 1 to 20 carbon atoms; an average value of $a_1$ and $a_2$ is approximately 0 to 10,000; and an average value of $b_1$ and $b_2$ is approximately 10 to 1,000; and $(A)_2Zn$ [Formula 2]

where A is a hydrocarbon group having 1 to 20 carbon atoms; and

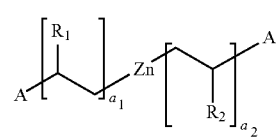
[Formula 3]

where $R_1$ and $R_2$ are each independently hydrogen or an alkyl group having 1 to 20 carbon atoms; A is a hydrocarbon group having 1 to 20 carbon atoms; and an average value of $a_1$ and $a_2$ ranges from approximately 0 to 10,000;

B—Li [Formula 4]

where B is an alkyl group having 1 to 20 carbon atoms;

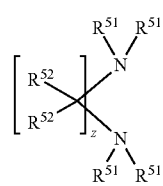
[Formula 5]

where $R^{51}$ and $R^{52}$ are each independently a hydrocarbon group having 1 to 20 carbon atoms, and z is an integer of approximately 2 or 3.

2. The method of claim 1, wherein the olefin monomer ($CH_2$=CH—R) is ethylene, propylene, 1-butene, 1-hexene, 1-octene, 1-decene or a mixture thereof, and the styrene-based monomer (ArCH=$CH_2$) is styrene.

3. The method of claim 1, wherein the olefin monomer ($CH_2$=CH—R) is a mixture of any one of propylene, 1-butene, 1-hexene and 1-octene; and ethylene, and the styrene-based monomer (ArCH=$CH_2$) is styrene.

4. The method of claim 1, wherein A of Formula 2 is one of a methyl group, an ethyl group, a hexyl group, a phenyl group and a benzyl group.

5. The method of claim 1, wherein the transition metal catalyst is a transition metal compound represented by Formula 6A or 6B below:

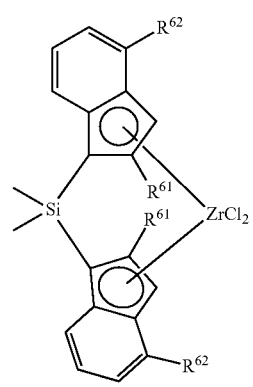
[Formula 6A]

In Formula 6A, $R^{61}$ is hydrogen or methyl, and $R^{62}$ is hydrogen or phenyl;

[Formula 6B]

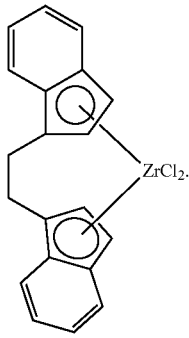

6. The method of claim 1, wherein the polymerization in the first step is performed by solution polymerization using a solvent containing one or more of isobutane, hexane, cyclohexane and methylcyclohexane.

7. The method of claim 1, wherein the alkyl lithium compound is n-BuLi.

8. The method of claim 1, wherein the amine ligand is a compound represented by Formula 5 is a compound in which $R^{51}$ is methyl, $R^{52}$ is hydrogen, and z is approximately 2.

9. The method of claim 1, wherein a molar ratio of the alkyl lithium compound and the amine ligand is approximately 1:0.5 to 1:1.5.

10. A composition prepared by the method of claim 1, comprising the organic zinc compound represented by the Formula 1:

[Formula 1]

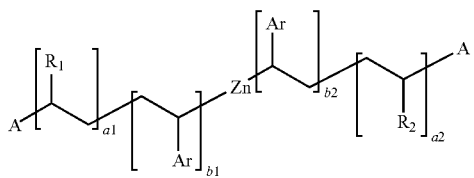

where $R_1$ and $R_2$ are each independently hydrogen or an alkyl group having 1 to 20 carbon atoms; Ar is an aryl group having 6 to 20 carbon atoms; A is a hydrocarbon group having 1 to 20 carbon atoms; an average value of $a_1$ and $a_2$ is approximately 0 to 10,000; and an average value of $b_1$ and $b_2$ is approximately 10 to 1,000, wherein a ratio of [(a number of polystyrene polymer chains)–(an amount of alkyl lithium)]/(an amount of zinc) is about 2.

11. The organic zinc compound of claim 10, wherein $R_1$ and $R_2$ of Formula 1 are each independently any one of hydrogen, a methyl group, an ethyl group, a butyl group, a hexyl group and an octyl group; Ar is a phenyl group; A is any one of a methyl group, an ethyl group, a hexyl group, a phenyl group and a benzyl group.

12. The organic zinc compound of claim 10, wherein the organic zinc compound is represented by Formula 1A below:

[Formula 1A]

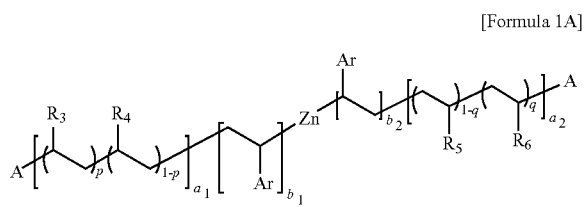

where $R_3$, $R_4$, $R_5$ and $R_6$ are each independently any one of hydrogen, a methyl group, an ethyl group, a butyl group, a hexyl group and an octyl group, $R_3$ and $R_4$ are not the same, $R_5$ and $R_6$ are not the same; Ar is a phenyl group; A is a methyl group, an ethyl group, a hexyl group, a phenyl group or a benzyl group; p and 1-p are mole fractions of respective repeating blocks constituting a repeating unit $a_1$, p ranges from approximately more than 0 less than 1; q and 1-q are mole fractions of respective repeating blocks constituting a repeating unit $a_2$, q ranges from approximately more than 0 less than 1; an average value of $a_1$ and $a_2$ is approximately more than 0 to 10,000; and an average value of $b_1$ and $b_2$ is approximately 10 to 1,000.

13. The organic zinc compound of claim 12, wherein any one of $R_3$ and $R_4$ of Formula 1A is hydrogen, and the other one is a methyl group, an ethyl group, a butyl group or a hexyl group; any one of $R_5$ and $R_6$ is hydrogen, and the other one is a methyl group, an ethyl group, a butyl group or a hexyl group.

* * * * *